United States Patent
Celeste et al.

(10) Patent No.: US 6,623,934 B2
(45) Date of Patent: Sep. 23, 2003

(54) BONE MORPHOGENETIC PROTEIN-16 (BMP-16) ANTIBODIES

(75) Inventors: Anthony J. Celeste, Hudson, MA (US); Beth L. Murray, Arlington, MA (US)

(73) Assignee: Genetics Institute, LLC., Cambridge, MA (US)

(*) Notice: Subject to any disclaimer, the term of this patent is extended or adjusted under 35 U.S.C. 154(b) by 0 days.

(21) Appl. No.: 09/994,177

(22) Filed: Nov. 26, 2001

(65) Prior Publication Data

US 2003/0158379 A1 Aug. 21, 2003

Related U.S. Application Data

(62) Division of application No. 09/328,775, filed on Jun. 9, 1999, now Pat. No. 6,331,612, which is a division of application No. 08/715,202, filed on Sep. 18, 1996, now Pat. No. 5,965,403.

(51) Int. Cl.[7] ................ C07K 16/00; C07K 16/18; C07K 16/24; C07K 16/26; G01N 33/53
(52) U.S. Cl. ............. 435/7.1; 530/387.1; 530/387.9; 530/388.1; 530/388.23; 530/388.24; 530/389.1; 530/389.2
(58) Field of Search ............. 530/387.1, 387.9, 530/388.1, 388.23, 388.24, 389.1, 389.2; 435/7.1

(56) References Cited

U.S. PATENT DOCUMENTS

| | | | |
|---|---|---|---|
| 5,013,649 A | | 5/1991 | Wang et al. |
| 5,106,748 A | | 4/1992 | Wozney et al. |
| 5,108,922 A | | 4/1992 | Wang et al. |
| 5,116,738 A | | 5/1992 | Wang et al. |
| 5,141,905 A | | 8/1992 | Rosen et al. |
| 5,187,076 A | | 2/1993 | Wozney et al. |
| 5,693,779 A | * | 12/1997 | Moos, Jr. et al. ......... 536/23.5 |
| 5,965,403 A | * | 10/1999 | Celeste et al. |
| 6,331,612 B1 | * | 12/2001 | Celeste et al. |

FOREIGN PATENT DOCUMENTS

| | | |
|---|---|---|
| WO | WO 91/18098 | 11/1991 |
| WO | WO 93/00432 | 1/1993 |
| WO | WO 93/16099 | 8/1993 |
| WO | WO 94/01557 | 1/1994 |
| WO | WO 94/15949 | 7/1994 |
| WO | WO 94/15965 | 7/1994 |
| WO | WO 95/15966 | 7/1994 |
| WO | WO 94/21681 | 9/1994 |
| WO | WO 94/26892 | 11/1994 |
| WO | WO 94/26893 | 11/1994 |
| WO | WO 95/01801 | 1/1995 |
| WO | WO 95/01802 | 1/1995 |
| WO | WO 95/10539 | 4/1995 |
| WO | WO 95/16035 | 6/1995 |
| WO | WO 96/01845 | 1/1996 |
| WO | WO 96/02559 | 2/1996 |

OTHER PUBLICATIONS

Schulz et al., Principles of Protein Structure, Springer–Verlag New York, Inc., New York, pp. 14–16, 1979.*
Zhou et al., Nature 361:543 (1993).
Conlon et al., Development 120:1919 (1994).
Conlon et al., Development 111:969 (1991).
Collignon, et al., Nature 381:155 (1996).
Lowe et al., Nature 381:158 (1996).
Broxmeyer et al., PNAS USA 85:9052 (1988).
Eto et al., Biochem. Biophys. Res. Comm. 142:1095 (1987).
Matzuk et al., Nature 360:313 (1992).
Ogawa et al., J. Biol. Chem. 267:14233 (1992).
Thies et al., J. Bone and Min. Res., 5:305 (1990).
Thies et al., Endocrinology 130:1318 (1992).

* cited by examiner

*Primary Examiner*—Elizabeth Kemmerer
(74) *Attorney, Agent, or Firm*—Finnegan, Henderson, Farabow, Garrett & Dunner, LLP.

(57) ABSTRACT

Purified BMP-16 proteins and processes for producing them are disclosed. DNA molecules encoding the BMP-16 proteins are also disclosed. The proteins may be used in the treatment of bone, cartilage, other connective tissue defects and disorders, including tendon, ligament and meniscus, in wound healing and related tissue repair, as well as for treatment of disorders and defects to tissues which include epidermis, nerve, muscle, including cardiac muscle, and other tissues and wounds, and organs such as liver, lung, cardiac, pancreas and kidney tissue. The proteins may also be useful for the induction of growth and/or differentiation of undifferentiated embryonic and stem cells.

10 Claims, No Drawings

BONE MORPHOGENETIC PROTEIN-16 (BMP-16)ANTIBODIES

This application is a divisional of Ser. No. 08/328,775, filed Jun. 9, 1999, now U.S. Pat. No. 6,331,612, which is a divisional of Ser. No. 08/715,302, filed Sep. 8, 1996, now U.S. Pat. No. 5,965,403.

The present invention relates to a novel family of purified proteins designated as Bone Morphogenetic Protein-16 (BMP-16) and BMP-16-related proteins, DNA encoding them, and processes for obtaining them. These proteins may be used to induce bone and/or cartilage or other connective tissue formation, and in wound healing and tissue repair. These proteins may also be used for augmenting the activity of other bone morphogenetic proteins.

BACKGROUND OF THE INVENTION

The search for the molecule or molecules responsible for the bone-, cartilage-, and other connective tissue-inductive activity present in bone and other tissue extracts has led to the discovery of a novel set of molecules called the Bone Morphogenetic Proteins (BMPs). The structures of several proteins., designated BMP-1 through BMP-15 have previously been elucidated. The unique inductive activities of these proteins, along with their presence in bone, suggests that they are important regulators of bone repair processes, and may be involved in the normal maintenance of bone tissue. There is a need to identify whether additional proteins, particularly human proteins, exist which play a role in these processes. The present invention relates to the identification of such a novel human protein, which the inventors have designated human BMP-16.

Human BMP-16 is the human homolog of a( murine protein called Nodal. The nucleotide and amino acid sequences of Nodal are described in Zhou et al., Nature, 361:543–547 (1993). The murine Nodal gene has been described as being expressed in the mouse node during gastrulation. A retrovirally induced insertional mutation of the murine Nodal gene results in the absence of mesodermal cell types normally associated with the primitive streak, and is embryonic lethal. Conlon et al., Development 120:1919–1928 (1994); Conlon et al., Development 111:969–981 (1991).

SUMMARY OF THE INVENTION

As used herein, the term BMP-16 protein refers to the human BMP-16 protein, having the amino acid sequence specified in SEQUENCE ID NO:2, as well as DNA sequences encoding the BMP-16 protein, such as the native human sequence shown in SEQUENCE ID NO: 1. Also included are naturally occurring allelic sequences of SEQUENCE ID NO: 1 and 2, and equivalent degenerative codon sequences of the above.

The BMP-16 DNA sequence (SEQ ID NO: 1) and amino acid sequence (SEQ ID NO: 2) are set forth in the Sequence Listings. BMP-16 proteins may be capable of inducing the formation of cartilage, bone, or other connective tissue, or combinations thereof. The cartilage and/or bone and/or other connective tissue activity in the rat bone formation assay described below. BMP-16 proteins may be further characterized by the ability to demonstrate effects upon the growth and/or differentiation of embryonic cells and/or stem cells. Thus, the proteins or compositions of the present invention may also be useful for treating cell populations such as embryonic cells or stem cell populations, to enhance or enrich the growth and/or differentiation of the cells.

Human BMP-16 protein may be produced by culturing a cell transformed with a DNA sequence comprising nucleotide a DNA sequence encoding the mature BMP-16 polypeptide, comprising nucleotide #511 to nucleotide #840 as shown in SEQ ID NO: 1, and recovering and purifying from the culture medium a protein characterized by the amino acid sequence comprising amino acids #1 to #110 as shown in SEQ ID NO:2 substantially free from other proteinaceous materials with which it is co-produced. For production in mammalian cells, the DNA sequence further comprises a DNA sequence encoding a suitable propeptide 5' to and linked in frame to the nucleotide sequence encoding the mature BMP-16-related polypeptide. The propeptide may be the native BMP-16-related propeptide or may be a propeptide from another protein of the TGF-β superfamily. Where the native BMP-16 propeptide is used, human BMP-16 may be produced by culturing a cell transformed with a DNA sequence comprising a DNA sequence encoding the full BMP-16, polypeptide, comprising nucleotide #1 to #840 as shown in SEQ ID NO: 1, producing a protein characterized by the amino acid sequence comprising amino acids #-170 to #110 as shown in SEQ ID NO:2, of which amino acids –170 to –1 comprise the native propeptide of human BMP-16, and recovering and purifying from the culture medium a protein characterized by the amino acid sequence comprising amino acids #1 to #110 as shown in SEQ ID NO:2, substantially free from other proteinaceous materials with which it is co-produced.

It is expected that other species, particularly human, have DNA sequences homologous to human BMP-16 protein. The invention, therefore, includes methods for obtaining the DNA sequences encoding human BMP-16 protein, the DNA sequences obtained by those methods, and the human protein encoded by those DNA sequences. This method entails utilizing the human BMP-16 protein nucleotide sequence or portions thereof to design probes to screen libraries for the corresponding gene from other species or coding sequences or fragments thereof from using standard techniques. Thus, the present invention may include DNA sequences from other species, which are homologous to human BMP-16 protein and can be obtained using the human BMP-16 sequence. The present invention may also include functional fragments of the human BMP-16 protein, and DNA sequences encoding such functional fragments, as well as functional fragments of other related proteins. The ability of such a fragment to function is determinable by assay of the protein in the biological assays described for the assay of the BMP-16 protein. A DNA sequence encoding the complete mature human BMP-16 protein (SEQ ID NO: 1) and the corresponding amino acid sequence (SEQ ID NO:2) are set forth herein. The BMP-16 proteins of the present invention, such as human BMP-16, may be produced by culturing a cell transformed with the correlating DNA sequence, such as the human BMP-16 DNA sequence, and recovering and purifying protein, such as BMP-16, from the culture medium. The purified expressed protein is substantially free from other proteinaceous materials with which it is co-produced, as well as from other contaminants. The recovered purified protein is contemplated to exhibit cartilage and/or bone and/or connective tissue formation activity. Thus, the proteins of the invention may be further characterized by the ability to demonstrate cartilage and/or bone and/or other connective tissue formation activity in the rat bone formation assay described below. BMP-16 proteins may be further characterized by the ability to demonstrated effects upon the growth and/or differentiation of embryonic cells and/or stem cells. Thus, the proteins or compositions of the present invention may also be characterized by their ability to enhance or enrich the growth and/or differentiation of the cells.

Another aspect of the invention provides pharmaceutical compositions containing a therapeutically effective amount of human BMP-16 protein, in a pharmaceutically acceptable vehicle or carrier. These compositions of the invention may be used in the formation of bone. These compositions may further be utilized for the formation of cartilage, or other connective tissue, including tendon, ligament, meniscus and other connective tissue, as well as combinations of the above, for example regeneration of the tendon-to-bone attachment apparatus. The compositions of the present invention such as compositions of human BMP-16, may also be used for wound healing and tissue repair. Compositions of the invention may further include at least one other therapeutically useful agent such as the BMP proteins BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748;:5,187,076; and 5,141,905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in PCT application WO 95/16035, or BMP-15, disclosed in co-pending patent application, Ser. No. 08/446,924, filed on May 18, 1995. Other compositions which may also be useful include Vgr-2, and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO993/16099. The disclosures of all of the above applications are hereby incorporated by reference.

The compositions of the invention may comprise, in addition to a BMP-16-related protein, other therapeutically useful agents including growth factors such as epidermal growth factor (EGF), fibroblast growth factor (FGF), transforming growth factor (TGF-α and TGF-β), activins, inhibins, and insulin-like growth factor (IGF). The compositions may also include an appropriate matrix for instance, for supporting the composition and providing a surface for bone and/or cartilage and/or other connective tissue growth. The matrix may provide slow release of the osteoinductive protein and/or the appropriate environment for presentation thereof.

The BMP-16 containing compositions may be employed in methods for treating a number of bone and/or cartilage and/or other connective tissue defects, periodontal disease and healing of various types of tissues and wounds. The tissue and wounds which may be treated include epidermis, nerve, muscle, including cardiac muscle, and other tissues and wounds, and other organs such as liver, lung, cardiac, pancreas and kidney tissue. These methods, according to the invention, entail administering to a patient needing such bone and/or cartilage and/or other connective tissue formation, wound healing or tissue repair, an effective amount of a BMP-16 protein. The BMP-16-containing compositions may also be used to treat or prevent such conditions as osteoarthritis, osteoporosis, and other abnormalities of bone, cartilage, muscle, tendon, ligament or other connective tissue, organs such as liver, lung, cardiac, pancreas and kidney tissue, and other tissues. These methods may also entail the administration of a protein of the invention in conjunction with at least one other BMP protein as described above. In addition, these methods may also include the administration of a BMP-16 protein with other growth factors including EGF, FGF, TGF-α, TGF-β, activin, inhibin and IGF.

Still a further aspect of the invention are DNA sequences coding for expression of a BMP-16 protein. Such sequences include the sequence of nucleotides in a 5' to 3' direction illustrated in SEQ ID NO: 1, DNA sequences which, but for the degeneracy of the genetic code, are identical to the DNA sequence SEQ ID NO: 1, and encode the protein of SEQ ID NO: 2. Further included in the present invention are DNA sequences which hybridize under stringent conditions with the DNA sequence of SEQ ID NO: 1 and encode a protein having the ability to induce the formation of cartilage and/or bone and/or other connective tissue, or other organs such as liver, lung, cardiac, pancreas and kidney tissue. Preferred DNA sequences include those which hybridize under stringent conditions [see, T. Maniatis et al, *Molecular Cloning (A Laboratory Manual)*, Cold Spring Harbor Laboratory (1982), pages 387 to 389]. It is generally preferred that such DNA sequences encode a polypeptide which is at least about 80% homologous, and more preferably at least about 90% homologous, to the mature human BMP-16 amino acid sequence shown in SEQ ID NO:2. Finally, allelic or other variations of the sequences of SEQ ID NO: 1, whether such nucleotide changes result in changes in the peptide sequence or not, but where the peptide sequence still has BMP-16 activity, are also included in the present invention. The present invention also includes fragments of the DNA sequence of BMP-16 shown in SEQ ID NO: 1 which encode a polypeptide which retains the activity of BMP-16 protein.

The DNA sequences of the present invention are useful, for example, as probes for the detection of mRNA encoding BMP-16 in a given cell population. Thus, the present invention includes methods of detecting or diagnosing genetic disorders involving the BMP-16 gene, or disorders involving cellular, organ or tissue disorders in which BMP-16 is irregularly transcribed or expressed. The DNA sequences may also be useful for preparing vectors for gene therapy applications as described below.

A further aspect of the invention includes vectors comprising a DNA sequence as described above in operative association with an expression control sequence therefor. These vectors may be employed in a novel process for producing a BMP-16 protein of the invention in which a cell line transformed with a DNA sequence encoding a BMP-16 protein in operative association with an expression control sequence therefor is cultured in a suitable culture medium and a BMP-16-related protein is recovered and purified therefrom. This process may employ a number of known cells both prokaryotic and eukaryotic as host cells for expression of the polypeptide. The vectors may be used in gene therapy applications. In such use, the vectors may be transfected into the cells of a patient ex vivo, and the cells may be reintroduced into a patient. Alternatively, the vectors may be introduced into a patient in vivo through targeted transfection.

Still a further aspect of the invention are BMP-16 proteins or polypeptides. Such polypeptides are characterized by having an amino acid sequence including the sequence illustrated in SEQ ID NO: 2, variants of the amino acid sequence of SEQ ID NO: 2, including naturally occurring allelic variants, and other variants in which the protein retains the ability to induce the formation of cartilage and/or bone and/or other connective tissue, or other organs such as liver, lung, cardiac, pancreas and kidney tissue, or other activity characteristic of BMP-16. Preferred polypeptides include a polypeptide which is at least about 80% homologous, and more preferably at least about 90% homologous, to the mature human BMP-16 amino acid sequence shown in SEQ ID NO:2. Finally, allelic or other variations of the sequences of SEQ ID NO: 2, whether such amino acid changes are: induced by mutagenesis, chemical alteration, or by alteration of DNA sequence used to produce the polypeptide, where the peptide sequence still has BMP-16 activity, are also included in the present invention. The present invention also includes fragments of the amino acid sequence of BMP-16 shown in SEQ ID NO: 2 which retain the activity of BMP-16 protein.

The purified proteins of the present inventions may be used to generate antibodies, either monoclonal or polyclonal, to human BMP-16 and/or other BMP-16-related proteins, using methods that are known in the art of antibody production. Thus, the present invention also includes antibodies to human BMP-16 and/or other related proteins. The antibodies may be useful for purification of BMP-16 and/or other BMP-16 related proteins, or for inhibiting or preventing the effects of BMP-16 related proteins. The BMP-16 protein and related proteins may be useful for inducing the growth and/or differentiation of embryonic cells and/or stem cells. Thus, the proteins or compositions of the present invention may also be useful for treating relatively undifferentiated cell populations, such as embryonic cells or stem cell populations, to enhance or enrich the growth and/or differentiation of the cells. The treated cell populations may be useful for implantation and for gene therapy applications.

Description of the Sequences

SEQ ID NO: 1 is a nucleotide sequence containing nucleotide sequence encoding the entire mature human BMP-16 polypeptide.

SEQ ID NO:2 is the amino acid sequence containing the mature human BMP-16 polypeptide sequence.

SEQ ID NO:3 is the nucleotide sequence of the second exon of the genomic DNA for the human BMP-16 polypeptide.

SEQ ID NO:4 is the nucleotide sequence of the third exon of the genomic DNA for the human BMP-16 polypeptide.

DETAILED DESCRIPTION OF THE INVENTION

The human BMP-16 sequence of the present invention is obtained using the whole or fragments of the murine BMP-16-related DNA sequence, or a partial human BMP-16 sequence, as a probe. Thus, the human BMP-16 DNA sequence comprise the DNA sequence of nucleotides #1 to #840 of SEQ ID NO: 1. This sequence of the human BMP-16 DNA sequence corresponds well to nucleotides #526 to #1393 of the murine Nodal DNA sequence described in GenBank accession #X70514. The human BMP-16 protein comprises the sequence of amino acids #–170 to #110 of SEQ ID NO: 2. The mature human BMP-16 protein is encoded by nucleotides #511 to #840 of SEQ ID NO: 1, and comprises the sequence of amino acids #1 to #110 of SEQ ID NO:2.

It is expected that human BMP-16 protein, as expressed by mammalian cells such as CHO cells, exists as a heterogeneous population of active species of BMP-16 protein with varying N-termini. It is expected that active species will comprise an amino acid sequence beginning with the cysteine residue at amino acid #10 of SEQ ID NO:2, or will comprise additional amino acid sequence further in the N-terminal direction. Thus, it is expected that DNA sequences encoding active BMP-16 proteins will comprise a nucleotide sequence comprising nucleotides #1, #511 or #538 to #837 or #840 of SEQ ID NO: 1. Accordingly, active species of human BMP-16 are expected to include those comprising amino acids #–170, #1 or #10 to #109 or #110 of SEQ ID NO:2.

A host cell may be transformed with a coding sequence encoding a propeptide suitable for the secretion of proteins by the host cell is linked in proper reading frame to the coding sequence for the mature BMP-16 protein. For example, see U.S. Pat. No. 5,168,050, in which a DNA encoding a precursor portion of a mammalian protein other than BMP-2 is fused to the DNA encoding a mature BMP-2 protein. See also the specification of WO95/16035, in which the propeptide of BMP-2 is fused to the DNA encoding a mature BMP-12 protein. The disclosure of both of these references are hereby incorporated by reference. Thus, the present invention includes chimeric DNA molecules comprising a DNA sequence encoding a propeptide from a member of the TGF-62 superfamily of proteins, other than BMP-16, is linked in correct reading frame to a DNA sequence encoding human BMP-16 protein, or a related protein. The term "chimeric" is used to signify that the propeptide originates from a different polypeptide than the BMP-16 protein The N-terminus of one active species of human BMP-16 is expected to be experimentally determined by expression in E. coli to be as follows: [M]HHLPDRSQLC corresponding to amino acids 1 to 10 of SEQ ID NO:1. Thus, it appears that the N-terminus of this species of BMP-16 is at amino acid #1 of SEQ ID NO: 1, and a DNA sequence encoding said species of BMP-16 would comprise nucleotides #511 to #840 of SEQ ID NO: 1. The apparent molecular, weight of human BMP-16 monomer is expected to be experimentally determined by SDS-PAGE to be approximately 13 kd on a Novex 16% tricine gel. The human BMP-16 protein is expected to exist as a clear, colorless solution in 0.1% trifluoroacetic acid.

It is expected that other BMP-16 proteins, as expressed by mammalian cells such as CHO cells, also exist as a heterogeneous population of active species of BMP-16-related protein with varying N-termini. For example, it is expected that active species of human BMP-16 protein will comprise an amino acid sequence beginning with the cysteine residue at amino acid #10 of SEQ ID NO:2, or will comprise additional amino acid sequence further in the N-terminal direction. Thus, it is expected that DNA sequences encoding active BMP-16 proteins include those which comprise a nucleotide sequence comprising nucleotides #511 or #538 to #837 or #840 of SEQ ID NO: 1. Accordingly, active human BMP-16 proteins include those comprising amino acids #1 or #10 to #109 or 110 of SEQ ID NO: 2.

The BMP-16 proteins of the present invention, include polypeptides having a molecular weight of about 13 kd in monomeric form, said polypeptide comprising the amino acid sequence of SEQ ID NO: 2 and having the ability to induce the formation of cartilage and/or bone and/or other connective tissue in the Rosen-Modified Sampath-Reddi ectopic implant assay, described in the examples.

The BMP-16 proteins recovered from the culture medium are purified by isolating them from other proteinaceous materials from which they are co-produced and from other contaminants present. BMP-16 proteins may be characterized by the ability to induce the formation of cartilage and/or bone and/or other connective tissue and other tissue repair and differentiation, for example, in the rat bone formation assay described below. In addition BMP-16 proteins may be further characterized by their effects upon the growth and/or differentiation of embryonic cells and/or stem cells. Thus, the proteins or compositions of the present invention may be characterized by the embryonic stem cell assay described below.

The BMP16 proteins provided herein also include factors encoded by the sequences similar to those of SEQ ID NO: 1, but into which modifications or deletions are naturally provided (e.g. allelic variations in the nucleotide sequence which may result in amino acid changes in the polypeptide) or deliberately engineered. For example, synthetic polypeptides may wholly or partially duplicate continuous sequences of the amino acid residues of SEQ ID NO:2. These sequences, by virtue of sharing primary, secondary, or tertiary structural and conformational characteristics with bone growth factor polypeptides of SEQ ID NO: 2 may possess biological properties in common therewith. It is know, for example that numerous and conformation of a protein, thus maintaining the biological properties as well. For example, it is recognized that conservative amino acid substitutions may be made among amino acids with basic side chains, such as lysine (Lys or K), arginine (Arg or R) and histidine (His or H) amino acids with acidic side chains, such as aspartic acid (Asp or D) and glutanuc acid (Glu or E); amino acids with uncharged polar side chains, such as asparagine (Asn or N), glutamine (Gln or Q), serine (Ser or S), threonine (Thr, or T), and tyrosine (Tyr or Y); and amino acids with nonpolar side chains, such as alanine (Ala or A), glycine (Gly or G), valine (Val or V), leucine (Leu or L), isoleucine (Ile or I), proline (Pro or P), phenylalanine (Phe or F), methionine (Met or M), tryptophan (Trp or W) and cysteine (Cys or C). Thus, these modifications and deletions of the native BMP-16 may be employed as biologically active substitutes for naturally-occurring BMP-16 and other polypeptides in therapeutic processes. It can be readily determined whether a given variant of BMP-16 maintains the biological activity of BMP-16 by subjecting both BMP-16 and the variant of BMP-16 to the assays described in the examples.

Other specific mutations of the sequences of BMP-16 proteins described herein involve modifications of glycosylation sites. These modifications may involve O-linked or N-linked glycosylation sites. For instance, the absence of glycosylation or only partial glycosylation results from amino acid substitution or deletion at asparagine-linked glycosylation recognition sites. The asparagine-linked glycosylation recognition sites comprise tripeptide sequences which are specifically recognized by appropriate cellular glycosylation enzymes. These tripeptide sequences are either asparagine-X-threonine or asparagine-X-serine, where X is usually any amino acid. A variety of amino acid substitutions or deletions at one or both of the first or third amino acid positions of a glycosylation recognition site (and/or amino acid deletion at the second position) results in non-glycosylation at the modified tripeptide sequence. Additionally, bacterial expression of BMP-16-related protein will also result in production of a non-glycosylated protein, even if the glycosylation sites are left unmodified.

The present invention also encompasses the novel DNA sequences, free of association with DNA sequences encoding other proteinaceous materials, and coding for expression of BMP-16 proteins. These DNA sequences include those depicted in SEQ ID NO: 1 in a 5' to 3' direction and those sequences which hybridize thereto under stringent hybridization washing conditions [for example, 0.1×SSC, 0.1% SDS at 65° C.; see, T. Maniatis et al, *Molecular Cloning (A Laboratory Manual)*, Cold Spring Harbor Laboratory (1982), pages 387 to 3891] and encode a protein having cartilage and/or bone and/or other connective tissue inducing activity. These DNA sequences also include those which comprise the DNA sequence of SEQ ID NO: 1 and those which hybridize thereto under stringent hybridization conditions and encode a protein which maintain the other activities disclosed for BMP-16.

Similarly, DNA sequences which code for BMP-16 proteins coded for by the sequences of SEQ ID NO: 1, or BMP-16 proteins which comprise the amino acid sequence of SEQ ID NO: 2, but which differ in codon sequence due to the degeneracies of the genetic code or allelic variations (naturally-occurring base changes in the species population which may or may not result in an amino acid change) also encode the novel factors described herein. Variations in the DNA sequences of SEQ ID NO: 1 which are caused by point mutations or by induced modifications (including insertion, deletion, and substitution) to enhance the activity, half-life or production of the polypeptides encoded are also encompassed in the invention.

Another aspect of the present invention provides a novel method for producing BMP-16 proteins. The method of the present invention involves culturing a suitable cell line, which has been transformed with a DNA sequence encoding a BMP-16 protein of the invention, under the control of known regulatory sequences. The transformed host cells are cultured and the BMP-16 proteins recovered and purified from the culture medium. The purified proteins are substantially free from other proteins with which they are co-produced as well as from other contaminants.

Suitable cells or cell lines may be mammalian cells, such as Chinese hamster ovary cells (CHO). The selection of suitable mammalian host cells and methods for transformation, culture, amplification, screening, product production and purification are known in the art. See, e.g., Gething and Sambrook, *Nature*, 293:620–625 (1981), or alternatively, Kauftman et al, *Mol. Cell. Biol.*, 5(7):1750–1759 (1985) or Howley et al, U.S. Pat. No. 4,419,446. Another suitable mammalian cell line, which is described in the accompanying examples, is the monkey COS-1 cell line. The mammalian cell CV-1 may also be suitable.

Bacterial cells may also be suitable hosts. For example, the various strains of *E. coli* (e.g., HB101, MC1061) are well-known as host cells in the field of biotechnology. Various strains of *B. subtilis*, Pseudomonas, other bacilli and the like may also be employed in this method. For expression of the protein in bacterial cells, DNA encoding the propeptide of BMP-16 is generally not necessary.

Many strains of yeast cells known to those skilled in the art may also be available as host cells for expression of the polypeptides of the present invention. Additionally, where desired, insect cells may be utilized as host cells in the method of the present invention. See, e.g. Miller et al. *Genetic Engineering*, 8:277–298 (Plenum Press 1986) and references cited therein.

Another aspect of the present invention provides vectors for use in the method of expression of these novel BMP-16 polypeptides. Preferably the vectors contain the full novel DNA sequences described above which encode the novel factors of the invention Additionally, the vectors contain appropriate expression control sequences permitting expression of the BMP-16 protein sequences. Alternatively, vectors incorporating modified sequences as described above are also embodiments of the present invention. Additionally, the sequence of SEQ ID NO:1 or other sequences encoding BMP-16 proteins could be manipulated to express a mature BMP-16 protein by deleting BMP-16 propeptide sequences and replacing them with sequences encoding the complete propeptides of other BMP proteins or members of the TGF-β superfamily. Thus, the present invention includes chimeric DNA molecules encoding a propeptide from a member of the TGF-β superfamily linked in correct reading frame to a DNA sequence encoding a BMP-16 polypeptide.

The vectors may be employed in the method of transforming cell lines and contain selected regulatory sequences in operative association with the DNA coding sequences of the invention which are capable of directing the replication and expression thereof in selected host cells. Regulatory sequences for such vectors are known to those skilled in the art and may be selected depending upon the host cells. Such selection is routine and does not form part of the present invention.

A protein of the present invention, which induces cartilage and/or bone and/or other connective tissue formation in circumstances where such tissue is not normally formed, has application in the healing of bone fractures and cartilage or other connective tissue defects in humans and other animals. Such a preparation employing a BMP-16 protein may have prophylactic use in closed as well as open fracture reduction and also in the improved fixation of artificial joints. De novo bone formation induced by an osteogenic agent contributes to the repair of congenital trauma induced, or oncologic resection induced craniofacial defects, and also is useful in cosmetic plastic surgery. A BMP-16-related protein may be used in the treatment of periodontal disease, and in other tooth repair processes. Such agents may provide an environment to attract bone-forming cells, stimulate growth of bone-forming cells or induce differentiation of progenitors of bone-forming cells, and may also support the regeneration of the periodontal ligament and attachment apparatus, which connects bone and teeth. BMP-16 polypeptides of the invention may also be useful in the treatment of osteoporosis. A variety of osteogenic, cartilage-inducing and bone inducing factors have been described. See, e.g., European patent applications 148,155 and 169,016 for discussions thereof.

The proteins of the invention may also be used in wound healing and related tissue repair. The types of wounds include, but are not limited to burns, incisions and ulcers. (See, e.g. PCT Publication WO84/01106 for discussion of wound healing and related tissue repair). It is further contemplated that proteins of the invention may increase neuronal, astrocytic and glial cell survival and therefore be useful in transplantation and treatment of conditions exhibiting a decrease in neuronal survival and repair. The proteins of the invention may further be useful for the treatment of conditions related to other types of tissue, such as nerve, epidermis, muscle, and other organs such as liver, lung, cardiac, pancreas and kidney tissue. The proteins of the present invention may farther be useful for the treatment of relatively undifferentiated cell populations, such as embryonic cells, or stem cells, to enhance growth and/or differentiation of the cells. The proteins of the present invention may also have value as a dietary supplement, or as a component of cell culture media. For this use, the proteins may be used in intact form, or may be predigested to provide a more readily absorbed supplement.

The proteins of the invention may also have other useful properties characteristic of the TGF-β superfamily of proteins. Such properties include antigenic, chemotactic and/or chemoattractant properties, and effects on cells including induction of collagen synthesis, fibrosis, differentiation responses, cell proliferative responses and responses involving cell adhesion, migration and extracellular matrices. These properties make the proteins of the invention potential agents for wound healing, reduction of fibrosis and reduction of scar tissue formation.

When dimerized as a homodimer or as a heterodimer with other BMPs, with other members of the TGF-β superfamily of proteins, or with inhibin-α proteins or inhibin-β proteins, the BMP-16 heterodimer is expected to demonstrate, effects on the production of follicle stimulating hormone (FSH), as described further herein. It is recognized that FSH stimulates the development of ova in mammalian ovaries (Ross et al., in Textbook of Endocrinology, ed Williams, p. 355 (1981) and that excessive stimulation of the ovaries with FSH will lead to multiple ovulations. FSH is also important in testicular function. Thus, BMP-16 may be useful as a contraceptive based on the ability of inhibins to decrease fertility in female mammals and decrease spermatogenesis in male mammals. Administration of sufficient amounts of other inhibins can induce infertility in mammals. BMP-16 may also be useful as a fertility inducing therapeutic, based upon the ability of activin molecules in stimulating FSH release from cells of the anterior pituitary. See, for example, U.S. Pat. No. 4,798,885. BMP-16 may also be useful for advancement of the onset of fertility in sexually immature mammals, so as to increase the lifetime reproductive performance of domestic animals such as cows, sheep and pigs. It is further contemplated that BMP-16 may be useful in modulating hematopoiesis by inducing the differentiation of etyttroid cells [see, e.g., Broxmeyer et al, *Proc. Natl. Acad. Sci. USA*. 85:9052–9056 (1988) or Eto et al, *Biochem. Biophys. Res. Comm.*, 142:1095–1103 (1987)], for suppressing the development of gonadal tumors [see, e.g., Matzuk et al., *Nature*, 360:313–319 (11992)] or for augmenting the activity of bone morphogenetic proteins [see, e.g., Ogawa et al., *J. Biol. Chem.*, 267:14233–14237 (1992)].

BMP-16 proteins may be further characterized by their ability to modulate the release of follicle stimulating hormone (FSH) in established in vitro bioassays using rat anterior pituitary cells as described [see, e.g., Vale et al, *Endocrinology*, 91:562–572 (1972); Ling et al., *Nature*, 321:779–782 (1986) or Vale et al., *Nature*, 321:776–779 (1986)]. It is contemplated that the BMP-16 protein of the invention, when composed as a heterodimer with inhibin α or inhibin β chains, will exhibit regulatory effects, either stimulatory or inhibitory, on the release of follicle stimulating hormone (FSH), from anterior pituitary cells as described [Ling et al., *Nature*, 321:779–782 (1986) or Vale et al., *Nature*, 321:776–779 (1986); Vale et al, *Endocrinology*, 91:562–572 (1972). Therefore, depending on the particular composition, it is expected that the BMP-16 protein of the invention may have contrasting and opposite effects on the release of follicle stimulating hormone (FSH) from the anterior pituitary.

Activin A (the homodimeric composition of inhibin $β_A$) has been shown to have erythropoietic-stimulating activity [see e.g. Eto et al., *Biochem. Biophys. Res. Commun.*, 142:1095–1103 (1987) and Murata et al., *Proc. Natl. Acad. Sci. U.S.A.*, 85:2434–2438 (1988) and Yu et al., *Nature*, 330:765–767 (1987)]. It is contemplated that the BMP-16 protein of the invention may have a similar erythropoietic-stimulating activity. This activity of the BMP-16 protein may be further characterized by the ability of the BMP-16 protein to demonstrate erythropoietin activity in the biological assay performed using the human K-562 cell line as described by [Lozzio et al., *Blood*, 45:321–334 (1975) and U.S. Pat. No. 5,071,834].

A further aspect of the invention is a therapeutic method and composition for repairing fractures and other conditions related to cartilage and/or bone and/or other connective tissue defects or periodontal diseases. The invention further comprises therapeutic methods and to compositions for wound healing and tissue repair. Such compositions comprise a therapeutically effective amount of at least one of the BMP-16-related proteins of the invention in admixture with a pharmaceutically acceptable vehicle, carrier or matrix. It is further contemplated that compositions of the invention may increase neuronal survival and therefore be useful in transplantation and treatment of conditions exhibiting a decrease in neuronal survival. Compositions of the invention may further include at least one other therapeutically useful agent, such as members of the TGF-β superfamily of proteins, which includes the BMP proteins BMP-1, BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; BMP-9, disclosed in PCT publication WO93100432; BMP-10, disclosed in PCT application WO94/26893; BMP-11, disclosed in PCT application WO94/26892, BMP-12 or BMP-13, disclosed in PCT application WO 95/16035, or BMP-15, disclosed in co-pending patent application, Ser. No. 08/446,924, filed on May 18, 1995. Other compositions which may also be useful include Vgr-2, and any of the growth and differentiation factors [GDFs], including those described in PCT applications WO94/15965; WO94/15949; WO95/01801; WO95/01802; WO94/21681; WO94/15966; WO95/10539; WO96/01845; WO96/02559 and others. Also useful in the present invention may be BIP, disclosed in WO94/01557; HP00269, disclosed in JP Publication number: 7-250688; and MP52, disclosed in PCT application WO93/16099. The disclosures of the above applications are hereby incorporated by reference herein.

It is expected that human BMP-16 protein may exist in nature as homodimers or heterodimers. To promote the formation of dimers of BMP-16 and useful proteins with increased stability, one can genetically engineer the DNA sequence of SEQUENCE ID NO: 1 to provide one or more additional cysteine residues to increase potential dimer formation. The resulting DNA sequence would be capable of producing a "cysteine added variant" of BMP-16. In a preferred embodiment, one would engineer the DNA sequence of SEQUENCE ID NO: 1 so that one or more codons may be altered to a nucleotide triplet encoding a cysteine residue, such as TGT or TGC. Alternatively, one can produce "cysteine added variants" of BMP-16 protein by altering the sequence of the protein at the amino acid level by altering one or more amino acid residues of SEQUENCE ID NO:2 to Cys. Production of "cysteine added variants" of proteins is described in U.S. Pat. No. 5,166,322, the disclosure of which is hereby incorporated by reference.

It is expected that the proteins of the invention may act in concert with or perhaps synergistically with other related proteins and growth factors. Further therapeutic methods and compositions of the invention therefore comprise a therapeutic amount of at least one BMP-16 protein of the invention with a therapeutic amount of at least one other member of the TGF-β superfamily of proteins, such as the BMP proteins disclosed in the applications described above. Such combinations may comprise separate molecules of the BMP proteins or heteromolecules comprised of different BMP moieties. For example, a method and composition of the invention may comprise a disulfide linked dimer comprising a BMP-16 protein subunit and a subunit from one of the "BMP" proteins described above. Thus, the present invention includes a purified BMP-16-related polypeptide which is a heterodimer wherein one subunit comprises the amino acid sequence from amino acid #1 to amino acid #110 of SEQ ID NO:2, and one subunit comprises an amino acid sequence for a bone morphogenetic protein selected from the group consisting of BMP-1, BMP-2, BMP-3, BMP-4, BMP-5, BMP-6, BMP-7, BMP-8, BMP-9, BMP-10, BMP-11, BMP-12 or BMP-13, disclosed in PCT application WO 95/16035, or BMP-15, disclosed in co-pending patent application, Ser. No. 08/446,924, filed on May 18, 1995. A further embodiment may comprise a heterodimer of BMP-16-related moieties, for example of human BMP-16 and the murine Nodal protein, which is the homologue of human BMP-16. Further, BMP-16 protein may be combined with other agents beneficial to the treatment of the bone and/or cartilage and/or other connective tissue defect, wound, or tissue in question. These agents include various growth factors such as epidermal growth factor (EGF), fibroblast growth factor (FGF), platelet derived growth factor (PDGF), transforming growth factors (TGF-α and TGF-β), activins, inhibins, and k-fibroblast growth factor (kFGF), parathyroid hormone (PTH), parathyroid hormone related peptide (PTHrP), leukemia inhibitory factor (LIB/HILA/DA), insulin-like growth factors (IGF-I and IGF-II). Portions of these agents may also be used in compositions of the present invention. The preparation and formulation of such physiologically acceptable protein compositions, having due regard to pH, isotonicity, stability and the like, is within the skill of the art. The therapeutic compositions are also presently valuable for veterinary applications due to the lack of species specificity in BMP proteins. Particularly domestic animals and thoroughbred horses in addition to humans are desired patients for such treatment with the BMP-16 proteins of the present invention.

The therapeutic method includes administering the composition topically, systemically, or locally as an implant or device. When administered, the therapeutic composition for use in this invention is, of course, in a pyrogen-free, physiologically acceptable form. Further, the composition may desirably be encapsulated or injected in a viscous form for delivery to the site of bone, cartilage or other connective tissue or other tissue damage. Topical administration may be suitable for wound healing and tissue repair. Therapeutically useful agents other than the BMP-16 proteins which may also optionally be included in the composition as described above, may alternatively or additionally, be administered simultaneously or sequentially with the BMP composition in the methods of the invention.

Preferably for bone and/or cartilage and/or other connective tissue formation, the composition includes a matrix capable of delivering BMP-16-related or other BMP proteins to the site of bone and/or cartilage and/or other connective tissue damage, providing a structure for the developing bone and cartilage and other connective tissue and optimally capable of being reabsorbed into the body. The matrix may provide slow release of BMP-16 protein and/or other bone inductive protein, as well as proper presentation and appropriate environment for cellular infiltration. Such matrices may be formed of materials presently in use for other implanted medical applications.

The choice of matrix material is based on biocompatibility, biodegradability, mechanical properties, cosmetic appearance and interface properties. The particular application of the BMP-16 compositions will define the appropriate formulation. Potential matrices for the compositions may be biodegradable and chemically defined calcium sulfate, tricalcium phosphate, hydroxyapatite, polylactic acid and polyanhydrides. Other potential materials are biodegradable and biologically well defined, such as bone or dermal collagen. Further matrices are comprised of pure proteins or extracellular matrix components. Other potential matrices are nonbiodegradable and chemically defined, such as sintered hydroxyapatite, bioglass, aluminates, or other ceramics. Matrices may be comprised of combinations of any of the above mentioned types of material, such as polylactic acid and hydroxyapatite or collagen and tricalcium phosphate. The bioceramics may be altered in composition, such as in calcium-aluminate-phosphate and processing to alter pore size, particle size, particle shape, and biodegradability.

The dosage regimen will be determined by the attending physician considering various factors which modify the action of the BMP-16 protein, e.g. amount of bone or other tissue weight desired to be formed, the site of bone or tissue damage, the condition of the damaged bone tissue, the size of a wound, type of damaged tissue, the patient's age, sex, and diet, the severity of any infection, time of administration and other clinical factors. The dosage may vary with the type of matrix used in the reconstitution and the types of BMP proteins in the composition. Generally, systemic or injectable administration will be initiated at a dose which is minimally effective, and the dose will be increased over a preselected time course until a positive effect is observed. Subsequently, incremental increases in dosage will be made limiting such incremental increases to such levels that produce a corresponding increase in effect, while taking into account any adverse affects that may appear. The addition of other known growth factors, such as IGF I (insulin like growth factor 1), to the final composition, may also effect the dosage.

Progress can be monitored by periodic assessment of bone or tissue growth and/or repair. The progress can be monitored, for example, x-rays, histomorphometric determinations and tetracycline labeling.

The following examples illustrate practice of the present invention in recovering and characterizing human BMP-16 and other BMP-16-related proteins, obtaining the human proteins and expressing the proteins via recombinant techniques.

EXAMPLES

Example 1

Isolation of DNA

DNA sequences encoding human BMP-16 and human BMP-16-related proteins may be isolated by various techniques known to those skilled in the art.

Based on the knowledge of BMP proteins and other proteins within the TGF-β family, it is predicted that the carboxyl-terminal portion of these molecules (mature peptide) would exhibit greater sequence conservation than the more amino-terminal portions (propeptide region). This sequence relationship between BMP proteins and other proteins within the TGF-β family enables those skilled in the art to design DNA probes from the carboxyl-terminal encoding portion (mature peptide encoding region) of these molecules which can be utilized to identify related BMP proteins and other proteins within the TGF-β family. As described below, the mature peptide encoding region of the murine nodal gene can be utilized to identify BMP-16 and BMP-16-related proteins.

A DNA probe corresponding to nucleotides #1060 through #1390 of the murine nodal gene (GenBank accession #X70514) can be radioactively labelled with $^{32}P$ and used to screen a human genomic library, under reduced stringency hybridization/washing conditions, to identify recombinant clones containing sequences of the human BMP-16 gene or sequences of other BMP-16 related genes.

Human BMP-16

One million recombinants of a human genomic library constructed in the vector λ DASH II (Stratagene catalog #945203) are plated at a density of approximately 20,000 recombinants per plate on 50 plates. Duplicate nitrocellulose replicas of the recombinant bacteriophage plaques are hybridized to the $^{32}p$ labelled 331 bp murine nodal DNA probe (described above) in standard hybridization buffer (5×SSC, 0.1% SDS, 5×Denhardt's, 100μg/ml salmon sperm DNA) under reduced stringency conditions (60° C. for approximately 2 days). On the second day of the hybridization, the radioactively labelled murine nodal DNA fragment containing hybridization solution is removed and the filters are washed under reduced stringency conditions (2×SSC, 0.1% SDS at 60° C.). The filters are wrapped in saran wrap and exposed to X-ray film for overnight to three days at −80° C., with the aid of an intensifying screen. The autoradiographs are developed and multiple positively hybridizing recombinants of various signal intensities are identified. These low stringency hybridization positive clones are plaque purified. Bacteriophage plate stocks of the plaque purified recombinants are made and bacteriophage DNA is isolated.

Individual positively hybridizing recombinant bacteriophage clones are examined for the presence of previously disclosed BMP sequences, or DNA sequences corresponding to other members of the TGF-β family, by hybridization to an array of oligonucleotides representative of these previously disclosed DNA sequences. The oligonucleotides which are used to define the previously disclosed BMP sequences and DNA sequences of other members of the TGF-β family have been immobilized to the surface of a glass chip. The template used for hybridization analysis to the immobilized oligonucleotide array is produced in the following manner:

Recombinant bacteriophage DNA derived from positively hybridizing human genomic clones identified through the use of the murine nodal probe (experiment described above) are subjected to specific DNA amplification. Oligonucleotide primers corresponding to DNA sequences of the of the bacteriophage cloning vector λ DASH II are utilized to specifically amplify the human genomic DNA inserts of positively hybridizing recombinant clones. The following oligonucleotide primers are designed on the basis of the sequence of the Lambda DASH II® genomic cloning vector (Stratagene Cloning Systems, Inc.; La Jolla, Calif.) and synthesized on an automated DNA synthesizer:

Oligonucleotide #1: ACTGCGCAACTCGTGAAAGG-TAGGC (SEQ ID NO:5)

Oligonucleotide #2: GAACACTCGTCCGAGAATAAC-GAGTGG (SEQ ID NO:6)

Oligonucleotides #1 and #2 are utilized as primers to allow the specific amplification of the human genomic DNA inserts of the recombinants identified by low stringency hybridization to the murine nodal probe or any recombinant DNA insert contained in the bacteriophage cloning vectors λ DASH II. The amplification reaction is performed as follows: Approximately 500 ng of purified recombinant bacteriophage DNA or an undetermined amount of recombinant bacteriophage DNA derived directly from an aqueous eluate of a purified bacteriophage plaque is added to a reaction mixture of 1×Perkin-Elmer Cetus GeneAmp® XL Buffer (catalog #N808-0180-comprised Tricine, Potassium Acetate, Glycerol and DMSO) with the supplementation of 250 μM each deoxynucleotide triphosphate (dATP, dGTP and dTTP), 90 μM DCTP, 30 μM Fluorescein-dCTP, 1.3 mM $Mg(OAc)_2$, 40 units/ml Perkin-Elmer Cetus rTth DNA polymerase (catalog #N808-0180), 400 nM oligonucleotide primer #1 and 400 nM oligonucleotide primer #2. The reaction mixture is subjected to thermal cycling in the following manner: 1 minute at 93° C. for one cycle, 40 seconds at 93° C. and 12 minutes at 68° C. for 30 cycles, followed by 10 minutes at 65° C. for one cycle. Approximately 1 μg of the DNA which is specifically amplified by this reaction is digested with 18 milliunits of RQ1 RNase-Free DNase (Promega Corp., Madison, Wis./Catalog #M6101 in 50 mM Tris-HCl pH 7.5, 10 mM $MgSO_4$ 50 mg bovine serum albumin (BSA)/ml, and 0.1 mM DTT at 37° for 90 minutes. The reaction is stopped with the addition of 0.1 volumes of 0.5 M $Na_2EDTA$. The fragmentation of the specifically amplified DNA under the conditions described above yields DNA fragments in the range of approximately 1500 to 50 base pairs. The 1500 to 50 bp specifically amplified DNA fragments are heat denatured at 95° C. for 10 minutes. The fragmented, denatured DNA solution is adjusted to a final concentration of 6×SSPE, 0.05% Triton X-100 and then hybridized to the BMP/TGF-β family representative oligonucleotide array which has been immobilized on a glass surface for a period of 4 hours to overnight at 37° C. The hybridized BMP/TGF-β family representative oligonucleotide array which has been immobilized on a glass surface is washed with 0.5×SSPE, 0.005% Triton X-100 and analyzed by a GeneChip 50 Scanner (Affymetrix).

One of the recombinant bacteriophage clones which hybridizes to the 329 bp murine nodal probe is designated λHG-NR35–1. Analysis of this clone utilizing the BMP/TGF-β family oligonucleotide array resulted in a positive hybridization pattern to a small subset of the oligonucleotides on the glass chip array. One of the oligonucleotides defined by a positive hybridization signal was utilized to determine the DNA sequence of the region of the human genomic insert which was responsible for the original hybridization signal to the murine nodal probe. The sequence of this oligonucleotide is set forth below:

Oligonucleotide #3: CTGTGAGGGCGAGTGTCC (SEQ ID NO:7)

This oligonucleotide which corresponds to nucleotides #1173–#1190 of the murine nodal sequence (Genbank Accession #X70514) was utilized to perform DNA sequence analysis of the λHG-NR35-1 genomic clone resulting in the identification of a portion of the human BMP-16 sequence disclosed in this application. The bacteriophage λHG-NR35-1 has been deposited with the American Type Culture Collection, 12301 Parklawn Drive, Rockville, Md. ATCC under the accession #97623 on Jun. 25, 1996. This deposit meets the requirements of the Budapest Treaty of the International Recognition of the Deposit of Microorganisms for the Purpose of Patent Procedure and Regulations thereunder. The hybridizing region of this recombinant, λHG-NR35-1, is localized to two BamHII fragments of approximately 2.1 kilobases (kb) and 4.3 kb in length. Each of these fragments are individually subcloned into the plasmid vector pGEM-3.

The plasmid subclones containing the 2.1 kb and 4.3 kb BamHI fragments are designated DH5α/pGEM#-NR35-1#B2 and DH5α/pGEM#-NR35-1#B18, respectively. The plasmid subclone containing the 2.1 kb BamHI hybridizing fragment (DH5α/pGEM#-NR35-1#B2) has been deposited with the ATCC under the accession #98085 on Jun. 25, 1996. The plasmid subclone containing the 4.3 kb BamHI hybridizing fragment (DH5α/pGEM#-NR35-1#B18) has been deposited with the ATCC under the accession #98084 on Jun. 25, 1996. These deposits meet the requirements of the Budapest Treaty of the International Recognition of the Deposit of Microorganisms for the Purpose of Patent Procedure and Regulations thereunder. The DNA sequence of a portion of the 2.1 kb insert of the plasmid subclone, DH5α/pGEM#-NR35-1#B2, is set forth in SEQ ID NO:3. A portion of this sequence (nucleotides #383 to #1080) represents exon 2 of the human BMP-16 gene as defined by comparison to exon 2 of the murine nodal gene (nucleotides #524 through #1240 of GenBank Accession No. X70514. The DNA sequence of a portion of the 4.3 kb insert of the plasmid subclone, DH5α/pGEM#-NR35-1#B18, is set forth in SEQ ID NO:4. A portion of this sequence (nucleotides #434 to #583) represents the coding region of exon 3 of the human BMP-16 gene as defined by comparison to the protein coding sequence of exon 3 of the murine nodal gene (nucleotides #1241 through #1390 of GenBank Accession No. X70514. Based on the knowledge of the murine nodal gene structure, the specific protein coding nucleotide sequences contained therein, and the comparisons of those sequences to sequences contained within exon 2 (SEQ ID NO:3) and exon 3 (SEQ ID NO:4) of the human BMP-16 gene which have been detailed above; one can compile a partial coding sequence for the human BMP-16 protein of the invention. This partial human BMP-16 coding sequence (from which intervening sequences/introns and other non-BMP-16 protein encoding sequences of SEQ ID NOs: 3 and 4 have been removed) is set forth in SEQ ID NO: 1. The compiled sequence predicted from the fusion of the coding sequences from exons 2 and 3 of the human BMP-16 gene defines an open reading frame of 840 nucleotides (nucleotides #1 through #840 of SEQ ID NO: 1) which encodes 280 amino acids of the human BMP-16 protein of the invention. The encoded 280 amino acid BMP-16 protein set forth in SEQ ID NO:2 includes the full mature human BMP-16 peptide (amino acids #1–#110 of SEQ ID NO:2), as well as the C-terminal portion of the BMP-16 propeptide (amino acids #-170 through #-1 of SEQ ID NO:2

Based on the knowledge of other BMP proteins and other proteins within the TGF-β family, it is predicted that the human BMP-16 precursor polypeptide would be cleaved at the multibasic sequence Arg-His-Arg-Arg corresponding to amino acids −4 to −10 (SEQ ID NO: 1) in agreement with a proposed consensus proteolytic processing sequence of Arg-X-X-Arg corresponding to amino acids −4 to −10 (SEQ ID NO: 1). Cleavage of the human BMP-16 precursor polypeptide is expected to generate a 110 amino acid mature peptide beginning with the amino acid His at position #1 of SEQ ID NO:2. The processing of human BMP-16 into the mature form is expected to involve dimerization and removal of the N-terminal region in a manner analogous to the processing of the related protein TGF-β [Gentry. et al., *Molec & Cell. Biol.*, 8:4162 (1988); Derynck et al. *Nature*, 316:701 (1985)].

It is contemplated therefore that the mature active species of human BMP-16 comprises a homodimer of two polypeptide subunits, each subunit comprising amino acids #1 to #110 of SEQ ID NO:2 with a predicted molecular weight of approximately 13,000 daltons. Further active species are contemplated comprising at least amino acids #10 to #110 of SEQ ID NO:2, thereby including the first conserved cysteine residue. As with other members of the TGF-β/BMP family of proteins, the carboxyl-terminal portion of the human BMP-16 protein exhibits greater sequence conservation than the more amino-terminal portion. The percent amino acid identity of the human BMP-16 protein in the cysteine-rich C-terminal domain (amino acids #10–#110 of SEQ ID NO:2) to the corresponding region of human BMP proteins and other proteins within the TGF-β family is as follows: BMP-2, 42%; BMP-3, 41%; BMP-4, 40%; BMP-5, 42%; BMP-6, 45%; BMP-7, 43%; BMP-8, 45%; BMP-9, 44%; BMP-10, 43%; BMP-11, 35%; BMP-12, 45%; BMP-13, 46%; BMP-15, 36%; Vg1, 44%; GDF-1, 38%; TGF-β1, 29%; TGF-β2, 32%; TGF-β3, 29%; inhibin $\beta_B$, 38%; inhibin $\beta_A$, 43%.

The human BMP-16 DNA sequence (SEQ ID NO:1), or a portion thereof, can be used as a probe to identify a human cell line or tissue which synthesizes human BMP-16 or a human BMP-16-related mRNA. Briefly described, RNA is extracted from a selected cell or tissue source and either electrophoresed on a formaldehyde agarose gel and transferred to nitrocellulose, or reacted with formaldehyde and spotted on nitrocellulose directly. The nitrocellulose is then hybridized to a probe derived from the coding sequence of human BMP-16.

Alternatively, the human BMP-16 sequence is used to design oligonucleotide primers which will specifically amplify a portion of the human BMP-16 or human BMP-16-related encoding sequence. It is contemplated that these human BMP-16 derived primers would allow one to specifically amplify corresponding human BMP-16 or BMP-16-related encoding sequences from mRNA, cDNA or genomic DNA templates. Once a positive source has been identified by one of the above described methods, mRNA is selected by oligo (dT) cellulose chromatography and cDNA is synthesized and cloned in λgt10 or other λ bacteriophage vectors known to those skilled in the art, for example, λZAP by established techniques (Toole et al., supra). It is also possible to perform the oligonucleotide primer directed amplification reaction, described above, directly on a pre-established human cDNA or genomic library which has been cloned into a bacteriophage vector. In such cases, a library which yields a specifically amplified DNA product encoding a portion of the human BMP-16 or BMP-16-related protein could be screened directly, utilizing the fragment of amplified human BMP-16 or BMP-16-related encoding DNA as a probe.

Additional methods known to those skilled in the art may be used to isolate other full-length cDNAs encoding human BMP-16-related proteins, or fill length cDNA clones encoding BMP-16-related proteins of the invention from species other than humans, particularly other mammalian species.

Example 2

W-20 BIOASSAYS

A. Description of W-20 Cells

Use of the W-20 bone marrow stromal cells as an indicator cell line is based upon the conversion of these cells to osteoblast-like cells after treatment with a BMP protein, [Thies et al, *Journal of Bone and Mineral Research*, 5:305 (1990); and Thies et al *Endocrinology*, 130:1318 (1992)]. Specifically, W-20 cells are a clonal bone marrow stromal cell line derived from adult mice by researchers in the laboratory of Dr. D. Nathan, Children's Hospital, Boston, Mass. Treatment of W-20 cells with certain BMP proteins results in (1) increased alkaline phosphatase production, (2) induction of PTH stimulated cAMP, and (3) induction of osteocalcin synthesis by the cells. While (1) and (2) represent characteristics associated with the osteoblast phenotype, the ability to synthesize osteocalcin is a phenotypic property only displayed by mature osteoblasts. Furthermore, to date we have observed conversion of W-20 stromal cells to osteoblast-like cells only upon treatment with BMPs. In this manner, the in vitro activities displayed by BMP treated W-20 cells correlate with the in vivo bone forming activity known for BMPs.

Below two in vitro assays useful in comparison of BMP activities of novel osteoinductive molecules are described.

B. W-20 Alkaline Phosphatase Assay Protocol

W-20 cells are plated into 96 well tissue culture plates at a density of 10,000 cells per well in 200 $\mu$l of media (DME with 10% heat inactivated fetal calf serum, 2 mM glutamine and 100 Units/ml penicillin+100 $\mu$g/ml streptomycin. The cells are allowed to attach overnight in a 95% air, 5% $CO_2$ incubator at 37° C. The 200 $\mu$l of media is removed from each well with a multichannel pipettor and replaced with an equal volume of test sample delivered in DME with 10% heat inactivated fetal calf serum, 2 mM glutamine and 1% penicillin-streptomycin. Test substances are assayed in triplicate. The test samples and standards are allowed a 24 hour incubation period with the W-20 indicator cells. After the 24 hours, plates are removed from the 37° C. incubator and the test media are removed from the cells. The W-20 cell layers are washed 3 times with 200 $\mu$l per well of calcium/magnesium free phosphate buffered saline and these washes are discarded. 50 $\mu$l of glass distilled water is added to each well and the assay plates are then placed on a dry ice/ethanol bath for quick freezing. Once frozen, the assay plates are removed from the dry ice/ethanol bath and thawed at 37° C. This step is repeated 2 more times for a total of 3 freeze-thaw procedures. Once complete, the membrane bound alkaline phosphatase is available for measurement. 50 $\mu$l of assay mix (50 mM glycine, 0.05% Triton X-100, 4 mM $MgCl_2$, 5 nM p-nitrophenol phosphate, pH=10.3) is added to each assay well and the assay plates are then incubated for 30 minutes at 37° C. in a shaking waterbath at 60 oscillations per minute. At the end of the 30 minute incubation, the reaction is stopped by adding 100 $\mu$l of 0.2 N NaOH to each well and placing the assay plates on ice. The spectrophotometric absorbance for each well is read at a wavelength of 405 nanometers. These values are then compared to known standards to give an estimate of the alkaline phosphatase activity in each sample. For example, using known amounts of p-nitrophenol phosphate, absorbance values are generated. This is shown in Table I.

TABLE I

Absorbance Values for Known Standards of P-Nitrophenol Phosphate

| P-nitrophenol phosphate umoles | Mean absorbance (405 nm) |
|---|---|
| 0.000 | 0 |
| 0.006 | 0.261 +/− .024 |
| 0.012 | 0.521 +/− .031 |
| 0.018 | 0.797 +/− .063 |
| 0.024 | 1.074 +/− .061 |
| 0.030 | 1.305 +/− .083 |

Absorbance values for known amounts of BMPs can be determined and converted to limoles of p-nitrophenol phosphate cleaved per unit time as shown in Table II.

TABLE II

Alkaline Phosphatase Values for W-20 Cells Treating with BMP-2

| BMP-2 concentration ng/ml | Absorbance Reading 405 nmeters | umoles substrate per hour |
|---|---|---|
| 0 | 0.645 | 0.024 |
| 1.56 | 0.696 | 0.026 |
| 3.12 | 0.765 | 0.029 |
| 6.25 | 0.923 | 0.036 |
| 12.50 | 1.121 | 0.044 |
| 25.0 | 1.457 | 0.058 |
| 50.0 | 1.662 | 0.067 |
| 100.0 | 1.977 | 0.080 |

These values are then used to compare the activities of known amounts of BMP-16 to BMP-2.

C. Osteocalcin RIA Protocol

W-20 cells are plated at 106 cells per well in 24 well multiwell tissue culture dishes in 2 mls of DME containing 10% heat inactivated fetal calf serum, 2 mM glutamine. The cells are allowed to attach overnight in an atmosphere of 95% air 5% $CO_2$ at 37° C. The next day the medium is changed to DME containing 10% fetal calf serum, 2 mM glutamine and the test substance in a total volume of 2 ml. Each test substance is administered to triplicate wells. The test substances are incubated with the W-20 cells for a total of 96 hours with replacement at 48 hours by the same test medias. At the end of 96 hours, 50 µl of the test media is removed from each well and assayed for osteocalcin production using a radioimmunoassay for mouse osteocalcin. The details of the assay are described in the kit manufactured by Biomedical Technologies Inc., 378 Page Street, Stoughton, Mass. 02072. Reagents for the assay are found as product numbers BT-431 (mouse osteocalcin standard), BT-432 (Goat anti-mouse Osteocalcin), BT-431 R (iodinated mouse osteocalcin), BT-415 (normal goat serum) and BT-414 (donkey anti goat IgG). The RIA for osteocalcin synthesized by W-20 cells in response to BMP treatment is carried out as described in the protocol provided by the manufacturer.

The values obtained for the test samples are compared to values for known standards of mouse osteocalcin and to the amount of osteocalcin produced by W-20 cells in response to challenge with known amounts of BMP-2. The values for BMP-2 induced osteocalcin synthesis by W-20 cells is shown in Table M.

TABLE III

Osteocalcin Synthesis by W-20 Cells

| BMP-2 Concentration ng/ml | Osteocalcin Synthesis ng/well |
|---|---|
| 0 | 0.8 |
| 2 | 0.9 |
| 4 | 0.8 |
| 8 | 2.2 |
| 16 | 2.7 |
| 31 | 3.2 |
| 62 | 5.1 |
| 125 | 6.5 |
| 250 | 8.2 |
| 500 | 9.4 |
| 1000 | 10.0 |

Example 3

Rosen Modified Sampath-Reddi Assay

A modified version of the rat bone formation assay described in Sampath and Reddi, *Proc. Natl. Acad. Sci. USA*, 80:6591–6595 (1983) is used to evaluate bone and/or cartilage and/or other connective tissue activity of BMP proteins. This modified assay is herein called the Rosen-modified Sampath-Reddi assay. The ethanol precipitation step of the Sampath-Reddi procedure is replaced by dialyzing (if the composition is a solution) or diafiltering (if the composition is a suspension) the fraction to be assayed against water. The solution or suspension is then equilibrated to 0.1% TFA. The resulting solution is added to 20 mg of rat matrix. A mock rat matrix sample not treated with the protein serves as a control. This material is frozen and lyophilized and the resulting powder enclosed in #5 gelatin capsules. The capsules are implanted subcutaneously in the abdominal thoracic area of 21–49 day old male Long Evans rats. The implants are removed after 7–14 days. Half of each implant is used for alkaline phosphatase analysis [see, Reddi et al, *Proc. Natl. Acad. Sci.*, 69:1601 (1972)].

The other half of each implant is fixed and processed for histological analysis. 1 µm glycolmethacrylate sections are stained with Von Kossa and acid fuschin to score the amount of induced bone and cartilage and other connective tissue formation present in each implant. The terms +1 through +5 represent the area of each histological section of an implant occupied by new bone and/or cartilage cells and matrix. A score of +5 indicates that greater than 50% of the implant is new bone and/or cartilage produced as a direct result of protein in the implant. A score of +4, +3, +2, and +1 would indicate that greater than 400%, 30%, 20% and 10% respectively of the implant contains new cartilage and/or bone.

Alternatively, the implants are inspected for the appearance of tissue resembling embryonic tendon, which is easily recognized by the presence of dense bundles of fibroblasts oriented in the same plane and packed tightly together. [Tendon/ligament-like tissue is described, for example, in Ham and Cormack, *Histology* (JB Lippincott Co. (1979), pp. 367–369, the disclosure of which is hereby incorporated by reference]. These findings may be reproduced in additional assays in which tendon/ligament-like tissues are observed in the BMP-16-related protein containing implants. The BMP-16-related proteins of this invention may be assessed for activity on this assay.

Example 4

Expression of BMP-16

In order to produce murine, human or other mammalian BMP-16-related proteins, the DNA encoding it is transferred into an appropriate expression vector and introduced into mammalian cells or other preferred eukaryotic or prokaryotic hosts by conventional genetic engineering techniques. The preferred expression system for biologically active recombinant human BMP-16 is contemplated to be stably transformed mammalian cells.

One skilled in the art can construct mammalian expression vectors by employing the sequence of SEQ ID NO: 1or SEQ ID NO: 3, or other DNA sequences encoding BMP-16-related proteins or other modified sequences and known vectors, such as pCD [Okayama et al., *Mol. Cell Biol.*, 2:161–170 (1982)], pJL3, pJL4 [Gough et al., *EMBO J.*, 4:645–653 (1985)] and pMT2 CXM.

The mammalian expression vector pMT2 CXM is a derivative of p91023(b) (Wong et al., Science 228:810–815, 1985) differing from the latter in that it contains the ampicillin resistance gene in place of the tetracycline resistance gene and further contains a XhoI site for insertion of cDNA clones. The functional elements of pMT2 CXM have been described (Kaufman, R. J., 1985, Proc. Natl. Acad. Sci. USA 2:689693) and include the adenovirus VA genes, the SV40 origin of replication including the 72 bp enhancer, the adenovirus major late promoter including a 5' splice site and the majority of the adenovirus tripartite leader sequence present on adenovirus late mRNAs, a 3' splice acceptor site, a DHFR insert, the SV40 early polyadenylation site (SV40), and pBR322 sequences needed for propagation in E. coli.

Plasmid pMT2 CXM is obtained by EcoRI digestion of pMT2-VWF, which has been deposited with the American Type Culture Collection (ATCC), Rockville, Md. (USA) under accession number ATCC 67122. EcoRI digestion excises the cDNA insert present in pMT2-VWF, yielding pMT2 in linear form which can be ligated and used to transform E. coli HB 101 or DH-5 to ampicillin resistance. Plasmid pMT2 DNA can be prepared by conventional methods. pMT2 CXM is then constructed using loopout/in mutagenesis [Morinaga, et al., Biotechnology 84: 636 (1984). This removes bases 1075 to 1145 relative to the Hind III site near the SV40 origin of replication and enhancer sequences of pMT2. In addition it inserts the following sequence:

5' PO-CATGGGCAGCTCGAG-3' (SEQ ID NO:8)

at nucleotide 1145. This sequence contains the recognition site for the restriction endonuclease XhoI. A derivative of pMT2CXM, termed pMT23, contains recognition sites for the restriction endonucleases PstI, Eco RI, SalI and XhoI. Plasmid pMT2 CXM and pMT23 DNA may be prepared by conventional methods.

pEMC2β1 derived from pMT21 may also be suitable in practice of the invention. pMT21 is derived from pMT2 which is derived from pMT2-VWF. As described above EcoRI digestion excises the cDNA insert present in pMT-VWF, yielding pMT2 in linear form which can be ligated and used to transform E Coli HB 101 or DH-5 to ampicillin resistance. Plasmid pMT2 DNA can be prepared by conventional methods.

pMT21 is derived from pMT2 through the following two modifications. First, 76 bp of the 5' untranslated region of the DHFR cDNA including a stretch of 19 G residues from G/C tailing for cDNA cloning is deleted. In this process, a XhoI site is inserted to obtain the following sequence immediately upstream from DHFR: 5'

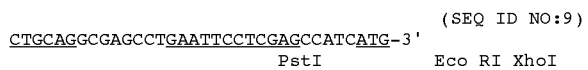
(SEQ ID NO:9)

Second, a unique ClaI site is introduced by digestion with EcoRV and XbaI, treatment with Klenow fragment of DNA polymerase I, and ligation to a ClaI linker (CATCGATG). This deletes a 250 bp segment from the adenovirus associated RNA (VAI) region but does not interfere with VAI RNA gene expression or function. pMT21 is digested with EcoRI and XhoI, and used to derive the vector pEMC2B 1.

A portion of the EMCV leader is obtained from pMT2-ECAT1 [S. K. Jung, et al, J. Virol 63:1651–1660 (1989)] by digestion with Eco RI and PstI, resulting in a 2752 bp fragment. This fragment is digested with TaqI yielding an Eco RI-TaqI fragment of 508 bp which is purified by electrophoresis on low melting agarose gel. A 68 bp adapter and its complementary strand are synthesized with a 5' TaqI protruding end and a 3' XhoI protruding end which has the following sequence:

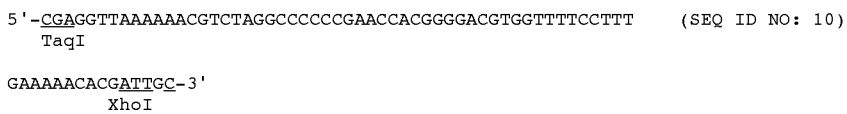

This sequence matches the EMC virus leader sequence from nucleotide 763 to 827. It also changes the ATG at position 10 within the EMC virus leader to an ATT and is followed by a XhoI site. A three way ligation of the pMT21 Eco RI-16hoI fragment, the EMC virus EcoRI-TaqI fragment, and the 68 bp oligonucleotide adapter TaqI-16hol adapter resulting in the vector pEMC2β1.

This vector contains the SV40 origin of replication and enhancer, the adenovirus major late promoter, a cDNA copy of the majority of the adenovirus tripartite leader sequence, a small hybrid intervening sequence, an SV40 polyadenylation signal and the adenovirus VA I gene, DHFR and β-lactamase markers and an EMC sequence, in appropriate relationships to direct the high level expression of the desired cDNA in mammalian cells.

The construction of vectors may involve modification of the BMP-16-related DNA sequences. For instance, BMP-16 cDNA can be modified by removing the non-coding nucleotides on the 5' and 3' ends of the coding region. The deleted non-coding nucleotides may or may not be replaced by other sequences known to be beneficial for expression. These vectors are transformed into appropriate host cells for expression of BMP-16-related proteins. Additionally, the sequence of SEQ ID NO: 1 or other sequences encoding BMP-16-related proteins can be manipulated to express a mature BMP-16-related protein by deleting BMP-16 encoding propeptide sequences and replacing them with sequences encoding the complete propeptides of other BMP proteins.

One skilled in the art can manipulate the sequences of SEQ ID NO: 1 by eliminating or replacing the mammalian regulatory sequences flanking the coding sequence with bacterial sequences to create bacterial vectors for intracellular or extracellular expression by bacterial cells. For example, the coding sequences could be further manipulated (e.g. ligated to other known linkers or modified by deleting non-coding sequences therefrom or altering nucleotides therein by other known techniques). The modified BMP-16-related coding sequence could then be inserted into a known bacterial vector using procedures such as described in T. Taniguchi et al., Proc. Natl Acad. Sci. USA, 77:5230–5233 (1980). This exemplary bacterial vector could then be transformed into bacterial host cells and a BMP-16-related protein expressed thereby. For a strategy for producing extracellular expression of BMP-16-related proteins in bacterial cells, see, e.g. European patent application EPA 177,343.

Similar manipulations can be performed for the construction of an insect vector [See, e.g. procedures described in published European patent application 155,476] for expression in insect cells. A yeast vector could also be constructed employing yeast regulatory sequences for intracellular or extracellular expression of the factors of the present invention by yeast cells. [See, e.g., procedures described in published PCT application WO86/00639 and European patent application EPA 123,289].

A method for producing high levels of a BMP-16-related protein of the invention in mammalian cells may involve the construction of cells containing multiple copies of the heterologous BMP-16-related gene. The heterologous gene is linked to an amplifiable marker, e.g. the dihydrofolate reductase (DHFR) gene for which cells containing increased gene copies can be selected for propagation in increasing concentrations of methotrexate (MTX) according to the procedures of Kaufinan and Sharp, *J. Mol. Biol.*, 159:601–629 (1982). This approach can be employed with a number of different cell types.

For example, a plasmid containing a DNA sequence for a BMP-16-related protein of the invention in operative association with other plasmid sequences enabling expression thereof and the DHFR expression plasmid pAdA26SV(A)3 [Kaufinan and Sharp, *Mol. Cell. Biol.*, 2:1304 (1982)] can be co-introduced into DHFR-deficient CHO cells, DUKX-BII, by various methods including calcium phosphate coprecipitation and transfection, electroporation or protoplast fusion. DHFR expressing transformants are selected for growth in alpha media with dialyzed fetal calf serum, and subsequently selected for amplification by growth in increasing concentrations of MTX (e.g. sequential steps in 0.02, 0.2, 1.0 and 5 $\mu$M MTX) as described in Kaufman et al., *Mol Cell Biol.*, 5:1750 (1983). Transformants are cloned, and biologically active BMP-16 expression is monitored by the Rosen-modified Sampath-Reddi rat bone formation assay described above in Example 3. BMP-16 protein expression should increase with increasing levels of MTX resistance. BMP-16 polypeptides are characterized using standard techniques known in the art such as pulse labeling with [35S] methionine or cysteine and polyacrylamide gel electrophoresis. Similar procedures can be followed to produce other related BMP-16-related proteins.

Example 5

Biological Activity of Expressed BMP-16

To measure the biological activity of the expressed BMP-16-related proteins obtained in Example 4 above, the proteins are recovered from the cell culture and purified by isolating the BMP-16-related proteins from other proteinaceous materials with which they are co-produced as well as from other contaminants. The purified protein may be assayed in accordance with the rat bone formation assay described in Example 3.

Purification is carried out using standard techniques known to those skilled in the art.

Protein analysis is conducted using standard techniques such as SDS-PAGE acrylamide [Laemmli, *Nature* 227:680 (1970)] stained with silver [Oakley, et al. *Anal. Biochem.* 105:361 (1980)] and by immunoblot [Towbin, et al. *Proc. Natl. Acad. Sci. USA* 76:4350 (1979)]

Example 6

Using Northern analysis, BMP-16 and BMP-16-related proteins can be tested for their effects on various cell lines. Suitable cell lines include cell lines derived from E13 mouse limb buds. After 10 days of treatment with BMP-16 or BMP-16-related protein, the cell phenotype is examined histologically for indications of tissue differentiation. In addition, Northern analysis of mRNA from BMP-16 or BMP-16-related protein treated cells can be performed for various markers including one or more of the following markers for bone, cartilage and/or tendon/ligament, as described in Table IV:

TABLE IV

| Marker | Bone | Cartilage | Tendon/Ligament |
| --- | --- | --- | --- |
| Osteocalcin | + | − | − |
| Alkaline Phosphatase | + | − | − |
| Proteoglycan Core Protein | +/−[1] | + | +[2] |
| Collagen Type I | + | + | + |
| Collagen Type II | +/−[1] | + | +[2] |
| Decorin | + | + | + |
| Elastin | +/−[3] | ? | + |

[1]Marker seen early, marker not seen as mature bone tissue forms
[2]Marker depends upon site of tendon; strongest at bone interface
[3]Marker seen at low levels Example 7

Embryonic Stem Cell Assay

In order to assay the effects of the BMP-16 proteins of the present invention, it is possible to assay the growth and differentiation effects in vitro on a number of available embryonic stem cell lines. One such cell line is ES-E14TG2, which is available from the American Type Culture Collection in Rockville, Md.

In order to conduct the assay, cells may be propagated in the presence of 100 units of LIF to keep them in an undifferentiated state. Assays are setup by first removing the LIF and aggregating the cells in suspension, in what is known as embryoid bodies. After 3 days the embryoid bodies are plated on gelatin coated plates (12 well plates for PCR analysis, 24 well plates for inmmunocytochemistry) and treated with the proteins to be assayed. Cells are supplied with nutrients and treated with the protein factor every 2–3 days. Cells may be adapted so that assays may be conducted in media supplemented with 15% Fetal Bovine Serum (FBS) or with CDM defined media containing much lower amounts of FBS.

At the end of the treatment period (ranging from 7–21 days) RNA is harvested from the cells and analyzed by quantitative multiplex PCR for the following markers: *Brachyury*, a mesodermal marker, AP-2, an ectodermal marker, and HNF-3α an endodermal marker. Through immunocytochemistry, it is also possible to detect the differentiation of neuronal cells (glia and neurons), muscle cells (cardiomyocytes, skeletal and smooth muscle), and various other phenotype markers such as proteoglycan core protein (cartilage), and cytokeratins (epidermis). Since these cells have a tendency to differentiate autonomously when LIF is removed, the results are always quantitated by comparison to an untreated control.

The foregoing descriptions detail presently preferred embodiments of the present invention. Numerous modifications and variations in practice thereof are expected to occur to those skilled in the art upon consideration of these descriptions. Those modifications and variations are believed to be encompassed within the claims appended hereto.

What is claimed is:

1. An antibody that binds a purified bone morphogenic protein-16 (BMP-16) polypeptide, wherein said BMP-16 comprises amino acids 1 to 110 of SEQ ID NO: 2, and wherein said antibody binds an epitope located in amino acids 1 to 110 of SEQ ID NO:2.

2. The antibody of claim 1, which is polyclonal.

3. The antibody of claim 1, which is monoclonal.

4. An antibody that binds a purified bone morphogenic protein-16 (BMP-16) polypeptide of claim 1, wherein the polypeptide is a dimer, wherein at least one subunit comprises amino acids 1 to 110 of SEQ ID NO: 2, and wherein said antibody binds an epitope located in amino acids 1 to 110 of SEQ ID NO:2.

5. The antibody of claim 4, which is polyclonal.

6. The antibody of claim 4, which is monoclonal.

7. A composition comprising the antibody of claim 1 or 4.

8. A method of purifying BMP-16 or BMP-16 related proteins comprising:

a) exposing said sample to the antibody of claim 1, 4, 2, 3, 5 or 6; and b) detecting binding of the antibody to the sample.

9. A method of determining the presence of a BMP-16 or BMP-16 related protein in a sample, comprising:

a) exposing said sample to the antibody of claim 1, 4, 2, 3, 5 or 6; and b) detecting binding of the antibody to the sample.

10. The method of claim 9, further comprising quantifying the amount of BMP-16 in the sample.

\* \* \* \* \*

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 843 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: sig_peptide
      (B) LOCATION: 1..510

(ix) FEATURE:
      (A) NAME/KEY: mat_peptide
      (B) LOCATION: 511..840

(ix) FEATURE:
      (A) NAME/KEY: CDS
      (B) LOCATION: 1..840

(xi) SEQUENCE DESCRIPTION: SEQ ID NO:1:

```
GTG GAT GGG CAG AAC TGG ACG TTT GCT TTT GAC TTC TCC TTC CTG AGC         48
Val Asp Gly Gln Asn Trp Thr Phe Ala Phe Asp Phe Ser Phe Leu Ser
-170              -165              -160              -155

CAA CAA GAG GAT CTG GCA TGG GCT GAG CTC CGG CTG CAG CTG TCC AGC         96
Gln Gln Glu Asp Leu Ala Trp Ala Glu Leu Arg Leu Gln Leu Ser Ser
         -150              -145              -140

CCT GTG GAC CTC CCC ACT GAG GGC TCA CTT GCC ATT GAG ATT TTC CAC        144
Pro Val Asp Leu Pro Thr Glu Gly Ser Leu Ala Ile Glu Ile Phe His
     -135              -130              -125

CAG CCA AAG CCC GAC ACA GAG CAG GCT TCA GAC AGC TGC TTA GAG CGG        192
Gln Pro Lys Pro Asp Thr Glu Gln Ala Ser Asp Ser Cys Leu Glu Arg
         -120              -115              -110

TTT CAG ATG GAC CTA TTC ACT GTC ACT TTG TCC CAG GTC ACC TTT TCC        240
Phe Gln Met Asp Leu Phe Thr Val Thr Leu Ser Gln Val Thr Phe Ser
    -105              -100               -95

TTG GGC AGC ATG GTT TTG GAG GTG ACC AGG CCT CTC TCC AAG TGG CTG        288
Leu Gly Ser Met Val Leu Glu Val Thr Arg Pro Leu Ser Lys Trp Leu
-90                -85                -80                -75

AAG CGC CCT GGG GCC CTG GAG AAG CAG ATG TCC AGG GTA GCT GGA GAG        336
Lys Arg Pro Gly Ala Leu Glu Lys Gln Met Ser Arg Val Ala Gly Glu
             -70                -65                -60

TGC TGG CCG CGG CCC CCC ACA CCG CCT GCC ACC AAT GTG CTC CTT ATG        384
Cys Trp Pro Arg Pro Pro Thr Pro Pro Ala Thr Asn Val Leu Leu Met
             -55                -50                -45

CTC TAC TCC AAC CTC TCG CAG GAG CAG AGG CAG CTG GGT GGG TCC ACC        432
Leu Tyr Ser Asn Leu Ser Gln Glu Gln Arg Gln Leu Gly Gly Ser Thr
         -40                -35                -30

TTG CTG TGG GAA GCC GAG AGC TCC TGG CGG GCC CAG GAG GGA CAG CTG        480
Leu Leu Trp Glu Ala Glu Ser Ser Trp Arg Ala Gln Glu Gly Gln Leu
    -25                -20                -15

TCC TGG GAG TGG GGC AAG AGG CAC CGT CGA CAT CAC TTG CCA GAC AGA        528
Ser Trp Glu Trp Gly Lys Arg His Arg Arg His His Leu Pro Asp Arg
-10                -5                  1                  5

AGT CAA CTG TGT CGG AAG GTC AAG TTC CAG GTG GAC TTC AAC CTG ATC        576
Ser Gln Leu Cys Arg Lys Val Lys Phe Gln Val Asp Phe Asn Leu Ile
             10                 15                 20
```

```
GGA TGG GGC TCC TGG ATC ATC TAC CCC AAG CAG TAC AAC GCC TAT CGC        624
Gly Trp Gly Ser Trp Ile Ile Tyr Pro Lys Gln Tyr Asn Ala Tyr Arg
            25                  30                  35

TGT GAG GGC GAG TGT CCT AAT CCT GTT GGG GAG GAG TTT CAT CCG ACC        672
Cys Glu Gly Glu Cys Pro Asn Pro Val Gly Glu Glu Phe His Pro Thr
        40                  45                  50

AAC CAT GCA TAC ATC CAG AGT CTG CTG AAA CGT TAC CAG CCC CAC CGA        720
Asn His Ala Tyr Ile Gln Ser Leu Leu Lys Arg Tyr Gln Pro His Arg
 55              60                  65                  70

GTC CCT TCC ACT TGT TGT GCC CCA GTG AAG ACC AAG CCG CTG AGC ATG        768
Val Pro Ser Thr Cys Cys Ala Pro Val Lys Thr Lys Pro Leu Ser Met
                    75                  80                  85

CTG TAT GTG GAT AAT GGC AGA GTG CTC CTA GAT CAC CAT AAA GAC ATG        816
Leu Tyr Val Asp Asn Gly Arg Val Leu Leu Asp His His Lys Asp Met
                90                  95                  100

ATC GTG GAA GAA TGT GGG TGC CTC TGA                                    843
Ile Val Glu Glu Cys Gly Cys Leu
            105                 110

(2) INFORMATION FOR SEQ ID NO:2:

(i) SEQUENCE CHARACTERISTICS:
        (A) LENGTH: 280 amino acids
        (B) TYPE: amino acid
        (D) TOPOLOGY: linear (ii) MOLECULE TYPE: protein (xi) SEQUENCE DESCRIPTION: SEQ ID NO:2:

Val Asp Gly Gln Asn Trp Thr Phe Ala Phe Asp Phe Ser Phe Leu Ser
-170                -165                -160                -155

Gln Gln Glu Asp Leu Ala Trp Ala Glu Leu Arg Leu Gln Leu Ser Ser
                -150                -145                -140

Pro Val Asp Leu Pro Thr Glu Gly Ser Leu Ala Ile Glu Ile Phe His
            -135                -130                -125

Gln Pro Lys Pro Asp Thr Glu Gln Ala Ser Asp Ser Cys Leu Glu Arg
        -120                -115                -110

Phe Gln Met Asp Leu Phe Thr Val Thr Leu Ser Gln Val Thr Phe Ser
    -105                -100                -95

Leu Gly Ser Met Val Leu Glu Val Thr Arg Pro Leu Ser Lys Trp Leu
-90                 -85                 -80                 -75

Lys Arg Pro Gly Ala Leu Glu Lys Gln Met Ser Arg Val Ala Gly Glu
                -70                 -65                 -60

Cys Trp Pro Arg Pro Thr Pro Pro Ala Thr Asn Val Leu Leu Met
            -55                 -50                 -45

Leu Tyr Ser Asn Leu Ser Gln Glu Gln Arg Gln Leu Gly Gly Ser Thr
        -40                 -35                 -30

Leu Leu Trp Glu Ala Glu Ser Ser Trp Arg Ala Gln Glu Gly Gln Leu
    -25                 -20                 -15

Ser Trp Glu Trp Gly Lys Arg His Arg His His Leu Pro Asp Arg
-10                 -5                    1                 5

Ser Gln Leu Cys Arg Lys Val Lys Phe Gln Val Asp Phe Asn Leu Ile
            10                  15                  20

Gly Trp Gly Ser Trp Ile Ile Tyr Pro Lys Gln Tyr Asn Ala Tyr Arg
        25                  30                  35

Cys Glu Gly Glu Cys Pro Asn Pro Val Gly Glu Glu Phe His Pro Thr
    40                  45                  50
```

```
Asn His Ala Tyr Ile Gln Ser Leu Leu Lys Arg Tyr Gln Pro His Arg
 55                  60                  65                  70

Val Pro Ser Thr Cys Cys Ala Pro Val Lys Thr Lys Pro Leu Ser Met
             75                  80                  85

Leu Tyr Val Asp Asn Gly Arg Val Leu Leu Asp His His Lys Asp Met
             90                  95                 100

Ile Val Glu Glu Cys Gly Cys Leu
        105                 110

(2) INFORMATION FOR SEQ ID NO:3:

(i) SEQUENCE CHARACTERISTICS:
        (A) LENGTH: 2002 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:
```

| | | | | | |
|---|---|---|---|---|---|
| GGGGAGGGGG | AGATGCAATT | CATCAACATA | TCCATGGACC | TCTTCTAGGA | TGTCCAAGTT | 60 |
| ATCTTGGGAA | GGGGGGATTG | GAAGAACAGT | AATTTCGGAG | TGTGGGTCTT | GGCAGTTGGG | 120 |
| CAAATCCAGG | TTTAAGTCTT | GGCTCTGCCA | CCTTCCAAGA | ATGACACCTT | GGTCAGATCT | 180 |
| TTTAACCACA | CTGAGCCTCA | GTTTTCCTCA | TCTCTAAAAG | GGACTCGAAA | ATCTTACCAA | 240 |
| CTCATAGAGT | TGGGGTGAGA | ATTCGAAGGT | AATTCTATAT | AAGGTAAGGC | CTCCAGCAAG | 300 |
| AGCTATGGTG | GTTGTGACAC | TGACTGAGGC | TGGGGGAGGC | CCTCACTCAC | CCTCCTTCCT | 360 |
| TCTTGGTTTT | CTCCTACCCA | GATGTGGCAG | TGGATGGGCA | GAACTGGACG | TTTGCTTTTG | 420 |
| ACTTCTCCTT | CCTGAGCCAA | CAAGAGGATC | TGGCATGGGC | TGAGCTCCGG | CTGCAGCTGT | 480 |
| CCAGCCCTGT | GGACCTCCCC | ACTGAGGGCT | CACTTGCCAT | TGAGATTTTC | CACCAGCCAA | 540 |
| AGCCCGACAC | AGAGCAGGCT | TCAGACAGCT | GCTTAGAGCG | GTTTCAGATG | GACCTATTCA | 600 |
| CTGTCACTTT | GTCCCAGGTC | ACCTTTTCCT | TGGGCAGCAT | GGTTTTGGAG | GTGACCAGGC | 660 |
| CTCTCTCCAA | GTGGCTGAAG | CGCCCTGGGG | CCCTGGAGAA | GCAGATGTCC | AGGGTAGCTG | 720 |
| GAGAGTGCTG | GCCGCGGCCC | CCCACACCGC | CTGCCACCAA | TGTGCTCCTT | ATGCTCTACT | 780 |
| CCAACCTCTC | GCAGGAGCAG | AGGCAGCTGG | GTGGGTCCAC | CTTGCTGTGG | GAAGCCGAGA | 840 |
| GCTCCTGGCG | GGCCCAGGAG | GGACAGCTGT | CCTGGGAGTG | GGGCAAGAGG | CACCGTCGAC | 900 |
| ATCACTTGCC | AGACAGAAGT | CAACTGTGTC | GGAAGGTCAA | GTTCCAGGTG | GACTTCAACC | 960 |
| TGATCGGATG | GGGCTCCTGG | ATCATCTACC | CCAAGCAGTA | CAACGCCTAT | CGCTGTGAGG | 1020 |
| GCGAGTGTCC | TAATCCTGTT | GGGGAGGAGT | TTCATCCGAC | CAACCATGCA | TACATCCAGG | 1080 |
| TGGGATGCCA | GGCGTGAGGG | GGAGGGGAGG | CAGTAAGCTG | GCCTTGGGGG | ACAGGGCTCT | 1140 |
| AGCTTTGCTA | TTAAATGACT | ATGTTCCTGT | ATTCACAGTT | ACTCAAGCAC | CTCCAATGTA | 1200 |
| CCAGGATCCT | GTGCTAGGTA | CCAGGCATGT | AGAGATGACC | GAGTGTAACA | TCCTTATAGA | 1260 |
| GCCTGTATGG | GGTCATGCGT | CACTGGGTAG | CCTTGAACAC | ATTGTTTCCC | TGGGACTTTA | 1320 |
| TCCTTGTCTT | TCATAAAATT | AGGGGGTGGG | GGTAGACCAG | AGGGTCTCAG | CACTTCCCTA | 1380 |
| GCCCTGACAT | TCTAGGAAAG | GAAGAATCTG | GACTTTGGGG | ACAGGCAGGC | CTGCATTTGA | 1440 |
| CTCCTCATTA | GCTGTGTGAT | ACTGTTTAGG | TTGCTTAATC | TCAAGCTTCA | GTTTTTCCAC | 1500 |
| CTGTAAGGAT | GAGGGAGGGC | AATGCCATAT | TTCAGAGGGG | ATGCTGTAGG | GGTTAATGAG | 1560 |
| ATGACATGCA | CATGGCATGT | AAAGCAGTTG | GTAGGTAACA | GGCATGTTTG | GCTGCATTAT | 1620 |

-continued

```
GGGGCCACGG TTGGAATCAC ACTGTTCCAG CCACAGTATT TTGGTTGAGA ATTGACTACC      1680

CATTCTACAG AAGTAGACAA GGCCAGCCAG GTGCGGTGGC ACATGCCTGA AATCCCAACA      1740

CTTTGGGAGG CTGAGGTGGG CGGATCACCT GAGGTCAGGA GTTCGAGACC AGCCTGACCA      1800

ACATGGTGAC ACCCCGTCTC TACTAAAAAT ACAAAAATCA GCCGGGTGTT GTGGCACATG      1860

CCTGTAATCC CAGCTACTCG GGAGGCTGAG GCAGGAGAAT CACTTGAACC CGGGAGGCAG      1920

AGATTGCAGT GAGCCGTGAT CAAGACCACT GCACTCCAGC CTGGGCAACA GAGCGAACTC      1980

CATCTCAAAA AACAAGAAAA AA                                               2002

(2) INFORMATION FOR SEQ ID NO:4:

(i) SEQUENCE CHARACTERISTICS:
        (A) LENGTH: 1184 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:4:

ATCACCTGAG CCCGGGAGGT TGAGGATGCA GTGAGCTGTG ATCAACACCA CTGCACTCCA        60

GCCTGGGCAA CAGAGCAAGA CCATCTCAAA AAGAAAAAA AAATTGGTAT TCCCTTTAGA       120

CTAGAATAAT AGGAGAACAT AAAAATTAGC TACCACTTAA AAAAAAAATT AGCTACTACT       180

CTACCCAGAT ACATGTAATT TTTTGAATCT GTTTAAAGGC TGTTTTCACA AAACAAGCAC       240

AGAGCTAAAG GTAGTTTAGA CATTAGAGTT CATGATATAT TGGCAAGCTA ATTCCTTTAT       300

GAAAATAATT TTCTGCTATT TTTGCACTCA GGAACTGACT TTAACTCCGT AACTTTTTTA       360

CTCTTTACCC AGAAATACTA TTCTGACCTG CCCATCAGGA TGTGAATTGA CACACCCTTC       420

CTTTCCTTTA CAGAGTCTGC TGAAACGTTA CCAGCCCCAC CGAGTCCCTT CCACTTGTTG       480

TGCCCCAGTG AAGACCAAGC CGCTGAGCAT GCTGTATGTG GATAATGGCA GAGTGCTCCT       540

AGATCACCAT AAAGACATGA TCGTGGAAGA ATGTGGGTGC CTCTGATGAC ATCCTGGAGG       600

GAGACTGGAT TTGCCTGCAC TCTGGAAGGC TGGGAAACTC CTGGAAGACA TGATAACCAT       660

CTAATCCAGT AAGGAGAAAC AGAGAGGGGC AAAGTTGCTC TGCCCACCAG AACTGAAGAG       720

GAGGGGCTGC CCACTCTGTA AATGAAGGGC TCAGTGGAGT CTGGCCAAGC ACAGAGGCTG       780

CTGTCAGGAA GAGGGAGGAA GAAGCCTGTG CAGGGGCTG GCTGGATGTT CTCTTTACTG        840

AAAAGACAGT GGCAAGGAAA AGCACAAGTG CATGAGTTCT TTACTGGATT TTTTAAAAAC       900

CTGTGAACCC CCCGAAACTG TATGTGAAAG TTGAGACATA TGTGCATGTA TTTTGGAGGT       960

GGGATGAAGT CACCTATAGC TTTCATGTAT TCTCCAAAGT AGTCTGTGTG TGACCTGTCC      1020

CCCTCCCCAA AGATTAAGGA TCACTGTATA GATTAAAAAG AGTCCGTCAA TCTCATTGCC      1080

TCAGGCTGGG TTGGGGAAC CCCACAGCTT TCTGGCTGGC CAGTGGCAAT CTACTGGCCT       1140

TGTCCAGAGG CTCACTGGAG TGGTTCTCTG CTAATGAGCT GTAC                      1184

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:5:
```

ACTGCGCAAC TCGTGAAAGG TAGGC                                         25

(2) INFORMATION FOR SEQ ID NO:6:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GAACACTCGT CCGAGAATAA CGAGTGG                                       27

(2) INFORMATION FOR SEQ ID NO:7:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

CTGTGAGGGC GAGTGTCC                                                 18

(2) INFORMATION FOR SEQ ID NO:8:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

CATGGGCAGC TCGAG                                                    15

(2) INFORMATION FOR SEQ ID NO:9:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

CTGCAGGCGA GCCTGAATTC CTCGAGCCAT CATG                               34

(2) INFORMATION FOR SEQ ID NO:10:

(i) SEQUENCE CHARACTERISTICS:
        (A) LENGTH: 68 base pairs
        (B) TYPE: nucleic acid
        (C) STRANDEDNESS: single
        (D) TOPOLOGY: linear -continued (ii) MOLECULE TYPE: DNA (genomic)

(xi) SEQUENCE DESCRIPTION: SEQ ID NO:10:

```
CGAGGTTAAA AAACGTCTAG GCCCCCCGAA CCACGGGGAC GTGGTTTTCC TTTGAAAAAC      60
ACGATTGC                                                              68
```